United States Patent [19]

Suzuki et al.

[11] Patent Number: 5,246,835
[45] Date of Patent: Sep. 21, 1993

[54] METHOD OF DIAGNOSING RENAL DISEASES

[75] Inventors: Hirokazu Suzuki, Kanagawa;
Yoshinori Sakurai, Sagamihara;
Yoshitami Ohashi, Hatano;
Masayoshi Goto, Isehara, all of Japan

[73] Assignee: Wakamoto Pharmaceutical Co., Ltd., Tokyo, Japan

[21] Appl. No.: 887,154

[22] Filed: May 22, 1992

[30] Foreign Application Priority Data

May 24, 1991 [JP] Japan .................................. 3-148080
Apr. 1, 1992 [JP] Japan .................................. 4-105214

[51] Int. Cl.$^5$ ................... G01N 33/543; G01N 33/68
[52] U.S. Cl. ..................................... 435/7.95; 435/7.5;
435/7.92; 436/63; 436/86; 436/166; 436/169;
436/513; 436/516; 436/811
[58] Field of Search ............... 436/166, 169, 86, 63,
436/516, 811, 513; 435/7.9, 7.92, 7.95, 7.5

[56] References Cited

U.S. PATENT DOCUMENTS 5,139,932 8/1992 Cederholm et al. ............... 435/7.95

OTHER PUBLICATIONS

Blatant et al., *Curr. Probe. Clin. Biochem.* (1979) 9:216-234.
Wiggins et al., *Clin. Chim Acta* (1985) 149:155-163.
Pharmacia (1982) *Isoelectrifocusing*, p. 1-5.
Pharmica (1983) *Affinity Chromatography*, pp. 1-13.
Schran, S. B., *The LDC Basic Book on Liquid Chromatrography*, (1981), pp. 1-19.
*Journal of Immunological Methods*, vol. 84, No. ½, 1985, Amsterdam, Netherlands, Koch et al., "A Simple Immunoblotting Method After Separation of Proteins in Agarose Gel", pp. 217-272.
*Analytical Chemistry*, vol. 61, No. 17, Sep. 1, 1989, Janis et al., "Dual-column Immunoassays Using Protein G Affinity Chromatography", pp. 1901-1906.
*The New England Journal of Medicine*, vol. 310, No. 6, Feb. 9, 1984, Boston, Mass., Mogensen, "Microalbuminuria Predicts Clinical Proteinuria and Early Mortality in Maturity-Onset Diabetes", pp. 356-360.
*Clinical Chemistry*, vol. 32, No. 7, Jul. 1986, Winston-Salem, NC; USA, Silver et al., "Immunoassays for Low Concentrations of Albumin in Urine", pp. 1303-1306.
*International Biotechnology Laboratory*, No. 4, Dec. 1983, Amsterdam, Netherlands, Di Bussolo et al., "HPLC: A Powerful Tool for Protein Analysis", pp. 52-59.

*Primary Examiner*—Mary E. Ceperley
*Attorney, Agent, or Firm*—Burns, Doane, Swecker & Mathis

[57] ABSTRACT

A method of diagnosing renal diseases by detecting fragments of albumin in human urine. The detection of the fragments is carried out by, for example, immunological methods or liquid chromatography techniques.

19 Claims, 10 Drawing Sheets

Elution patterns obtained by
TSK Gel G3000SW

Eluent: 0.55M Glycine-HCl pH3.0+0.15M NaCl +0.1%SDS

METHOD OF DIAGNOSING RENAL DISEASES

This application claims the priority of Japanese Patent Application Nos. Hei 3-148080 filed May 24, 1991 and Hei 4-105214 filed Apr. 1, 1992, which are incorporated herein by reference.

BACKGROUND OF THE INVENTION

1. Field of the Invention

This invention relates to a method of diagnosing renal diseases, more specifically to a method of diagnosing renal diseases by detecting albumin fragments in human urinary sample.

2. Prior Art

Clinical diagnosis of nephropathy, particularly diagnosis of diabetic nephropathy has conventionally been carried out by monitoring patient's conditions such as continuous proteinuria, renal dysfunction and hypertension, because renal biopsy is difficult. However, it is difficult to cure nephropathy of a patient discharging proteinuria, and such nephropathy generally develops into terminal renal insufficiency within 5 or 6 years. Therefore, in the field of the clinical medicine, it has been strongly desired to diagnose renal diseases and cure the diseases before they are found by the positive results of proteinuria test by conventional proteinuria test paper methods.

The determination method of urinary microalbumin has been developed as a diagnosing method of renal diseases for this purpose, and this method has recently become indispensable test method to the diagnosis of nephropathy. Accurate quantitative determination of urinary microalbumin may be carried out by, for instance, RIA (radioimmunoassay) and immunoprecipitation. Simple test kits for this determination are also commercially available and there can be used "ALBUSURE" (Eisai Co., Ltd.) as an example of those kits. The assay system of this commercially available kit is based on the agglutination inhibition technique, and the kit contains albumin-immunized latex and anti-albumin antibodies as test reagents. In the assay using this kit, the latex is agglutinated by the antigen-antibody reaction when albumin is substantially absent in the urinary sample whereas the latex is not agglutinated when the urinary sample contains albumin, which inhibits the antigen-antibody reaction.

As described above, methods of diagnosing renal diseases by determination of urinary microalbumin have been already known. However, urinary microalbumin of a patient indicates that the patient is in an early stage of nephropathy, which corresponds to the period of 6 to 20 years from the crisis of diabetes, and the nephropathy in such a stage is likely to develop into the forth stage of nephropathy (manifest nephropathy). (The stages of nephropathy are represented according to the classification of Mogensen, *N. Engl. J. Med.*, 310, 356, 1984.)

Therefore, there still remains a need to develop a method of diagnosing nephropathy, which enables the diagnosis of nephropathy in an earlier stage thereof.

SUMMARY OF THE INVENTION

Accordingly, the object of the present invention is to provide a method of diagnosing renal diseases, which enables the diagnosis at much earlier stage of the diseases as compared with conventional methods.

As a result of our intensive investigation, we have found that the above-described object of the present invention can be achieved by a method wherein fragments of albumin in human urinary samples are detected by, for instance, a combination of electrophoresis with immunoblot or liquid chromatography, and thus achieved the present invention.

Therefore, according to the present invention, there is provided a method of diagnosing renal diseases by detecting fragments of albumin in human urinary samples.

DESCRIPTION OF THE PREFERRED EMBODIMENTS

Figure 1:
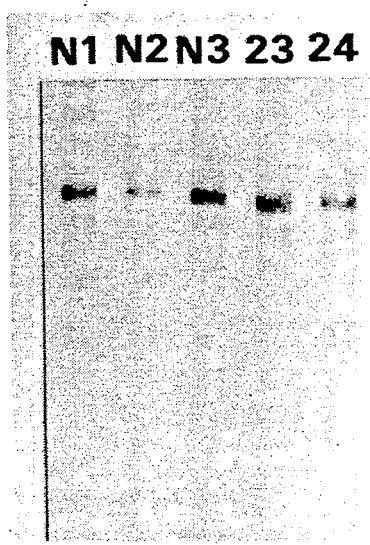
FIG. 1 is a photograph showing immunoblot patterns of urinary samples of 5 healthy control subjects analyzed by the present method (SDS-PAGE method).

The term "fragments of human albumin" or "human albumin fragments" herein used means all of the compounds obtained from degradation such as enzymatic degradation of human albumin in human serum and the compounds are composed of a molecular weight less than about 69,000, which is the molecular weight of native albumin.

In the method of the present invention, the albumin fragments may be firstly separated from native albumin molecule by utilizing differences in molecular weight or charge state between the human albumin fragments and the native albumin molecules and then the presence of the fragments is detected by utilizing, for instance, a specific antigen-antibody reaction.

For the detection of human albumin and the albumin fragments, immunological techniques based on specific antigen-antibody reaction are utilized. Examples of such immunological techniques include EIA (enzyme immunoassay), RIA and immunoblot techniques. Considering the operation efficiency of these techniques in combination with SDS polyacrylamide electrophoresis, cellulose acetate sheet electrophoresis, gel electrofocusing and the like, the most preferred technique is the immunoblot technique because of the excellent operability, the good rapidity and the like of this technique.

Further, the separation and detection of human albumin and the fragments thereof may be carried out by liquid chromatographic techniques.

The techniques for the separation and analysis of the albumin fragments are described hereinafter more in detail However, the following descriptions include only a part of the techniques useful for the present invention, and the present invention is not limited to those techniques to be described.

SDS Polyacrylamide Gel Electrophoresis

The SDS polyacrylamide gel electrophoresis (referred to as "SDS-PAGE" hereinafter) techniques useful for the present invention include both of the continuous buffer system reported by Shapiro et al. (*Biochem. Biophys. Res Commun.*, 28, 815, 1967) and Weber at al. (*J. Biol. Chem.*, 244, 4406, 1969) and the discontinuous buffer system reported by Laemmli (*Nature*, 277, 680, 1970). The discontinuous buffer system is preferred because of the excellent separation ability of this technique.

The concentration of the separation gel is not particularly limited as far as human albumin and the fragments can be separated from each other, and generally the used gel is one consisting a concentration of from about 5% to about 12.5% by weight.

Further, the SDS-PAGE method is classified into disc gel electrophoresis and slab gel electrophoresis. Both may be used for the present invention and slab gel electrophoresis is preferred.

Separated human albumin and the human albumin fragments are transferred to a support and visualised by utilizing an immunoblot method as follows.

After the separation by the SDS-PAGE method, human albumin and the fragments thereof contained in the gel are immediately transferred to a nitrocellulose sheet to be adsorbed on the sheet. The transferred proteins are reacted with first antibodies (anti-human albumin antibody in case of the present invention), then washed and reacted with enzyme-labeled second antibodies. After washing, the presence of the proteins are detected by adding an reagent for detecting the enzyme.

Various methods may be used for transferring the proteins and the most preferred transfer method is the method reported by Towbin et al. (*Proc. Natl. Acad. Sci.*, 76, 4350–4354, 1979).

Examples of the support on which the proteins are transferred, include nitrocellulose sheet, aminophenyl thioether sheet, aminobenzyloxymethyl sheet and diaminoethyl cellulose sheet. The most preferred support is a nitrocellulose sheet, and such a sheet is commercially available as, for example, BA85 (Schleicher & Schuell Co., Ltd.) and HAHY (Millipore Co., Ltd). Furthermore, it is convenient to use apparatuses and elements including SDS-polyacrylamide gel, electrophoresis apparatus, nitrocellulose sheet and transferring apparatus sold by the same manufacturer such as Tefco Co., Ltd.

When the antigen-antibody reaction is carried out on the nitrocellulose sheet, the non-specific reactions may be prevented with bovine serum albumin (BSA), skim milk and the like. Preferably, the non-specific reaction is prevented with skim milk, because of less cross-reactivity with the anti-human albumin antibodies.

The anti-human albumin antibodies can be easily obtained by immunizing a rabbit and it is also possible to use commercial products. Further, in order to prevent the nonspecific reactions, it is preferable to use the antibodies of a higher purity. The more purified antibody can be obtained by affinity chromatography.

The second antibodies are different depending on the animal species from which the anti-human albumin antibodies are obtained and those antibodies such as anti-rabbit IgG antibodies, anti-goat IgG antibodies, anti-mouse IgG antibodies are used. The second antibodies are preferably purified in the same way as the anti-human albumin antibodies in order to prevent the non-specific reactions.

Examples of the enzyme used for labeling of the second antibodies include peroxidase, alkaline phosphatase, glucose oxidase and the like. The most preferred enzyme is the peroxidase because pure peroxidase may be easily obtained and because the method for determining the activity thereof is sufficiently examined.

The second antibodies are easily labeled with enzymes according to the conventional methods reported by S. Arrameas (*Immunochemistry*, 6, 43, 1969) and P. K. Nakane and A. Kawaoi,(*J. Histochem. Cytochem.*, 22, 1084, 1974). The enzyme-labeled second antibodies are also commercially available from Cappel Co., Ltd. for the present invention.

As the reagent for detecting the peroxidase, there are a combination of aqueous hydrogen peroxide solution with diaminobenzidine, chloronaphthol, aminoethylcarbazole or the like, and the combination of aqueous hydrogen peroxide solution with diaminobenzidine is preferable. As the reagent for detecting the alkaline phosphatase, there are $\beta$-naphthylphosphoric acid, bromochloroindolylphosphoric acid and umbelliphenylphosphoric acid. As the reagent for detecting the glucose oxidase, there is D-glucose.

The procedure of the above-described SDS-PAGE method according to the present invention is summarized below, but the method of the present invention by SDS-PAGE is not limited thereby.

First of all, proteins contained in a urinary sample to be assayed are solubilized by treating the sample in boiled water for a certain period to inactivate the proteases contained in the sample and to efficiently denature the proteins with SDS and $\beta$-mercaptoethanol.

Then, the solubilized urinary sample is loaded on a lane of SDS-polyacrylamide slab gel in a certain amount and subjected to electrophoresis for a certain period by using tris/glycine buffer containing SDS as the electrophoresis buffer.

After the electrophoresis, the gel is equilibrated in preliminarily cooled tris/glycine buffer containing methanol (transfer buffer) for a certain period Then, the gel and the transfer support are mounted on a blotting apparatus so that the gel is positioned at cathode side and the transfer support at anode side. Transfer is carried out in a transfer bath containing transfer buffer at a constant voltage for a certain period under ice cooling.

After the transfer, the transfer support is washed with phosphate buffered saline (PBS) containing TWEEN 20 and subjected to a masking treatment with PBS containing skim milk at a constant temperature for a certain period.

Then the support is incubated with anti-human albumin antibodies diluted with PBS containing BSA at a constant temperature for a certain period.

After the reaction, the support is washed with PBS containing TWEEN 20 and incubated with enzyme-labeled second antibodies diluted with PBS containing BSA at a certain concentration at a constant temperature for a certain period to detect the albumin fragments.

Gel Electrofocusing Method

Separation of proteins by the gel electrofocusing is carried out in a medium having a pH gradient and the proteins were separated into each of the proteins according to the isoelectric point. The separation of proteins is based on the utilization of the behavior that an effective charge of ampholyte becomes 0 at a certain pH value and the ampholyte stops at that pH value in the pH gradient, whereas the proteins are separated by usual electrophoresis, utilizing differences of charging state of the electrolytes at a certain pH value.

The carrier for making the pH gradient is easily prepared from ampholyte (carrier ampholyte). The carrier ampholyte was developed by vesteber et al. (*Acta. Chem. Scand.*, 20, 820–834, 1966) and is commercially available from several manufacturers such as pharmacia Co., Ltd. with the trade name of Pharmalyte.

The support used for the gel electrofocusing should not show electroosmosis, and there can be used polyacrylamide gel as a typical example of such a support. The polyacrylamide gel normally functions as a molecular sieving too, and the molecular sieving effect deteriorates the separation when it is used in gel electrofocusing. Therefore, it is preferably used as a gel having a concentration not more than 5% by weight.

Preparation of the gel containing carrier ampholyte is described in various experiment manuals such as Y. Kono, H. Hirai and I. Sakurabayashi, "Experimental Procedures of Blotting Technique" 239-241, Softscience Co., Ltd., (1987). Commercially available slab gels such as IEF PAGE mini (registered trade mark of Tefco Co., Ltd.) are also useful for the present invention, and such commercial products are particularly convenient when a large number of samples should be analyzed.

While the conditions of the polyacrylamide gel electrofocusing are not particularly limited, it is normally carried out by using, as electrode solution, 0.1 to 1.0M sodium hydroxide for the cathode and 0.1 to 1.0M phosphoric acid for the anode. Test sample is dissolved in a solution containing the carrier ampholyte and glycerin to prepare a sample solution.

The electrofocusing is preferably carried out by varying the voltage from about 100 V to about 500 V.

After the electrofocusing, the concentrated protein in the gel is transferred to a support. Various supports such as nitrocellulose sheet, aminophenyl thioether sheet, aminobenzyloxymethyl sheet and diaminoethyl cellulose sheet can be used and the most preferred support is the nitrocellulose sheet. A nitrocellulose sheet is commercially available from several manufacturers, for example, BA85 (Schleicher & Schuell Co., Ltd.) and HAHY (Millipore Co., Ltd).

The transfer after the electrofocusing may be carried out according to, for instance, the method of Towbin et al. (*Proc. Natl. Acad. Sci.*, 76, 4350–4354, 1979) by using 0.5 to 1.0% by weight of acetic acid and by setting the gel and the sheet so that the sheet is positioned at the cathode side and the gel at the anode side.

The human albumin fragments transferred on the support such as a nitrocellulose sheet under the electric currency may be detected by the same procedure as used in the SDS-PAGE method.

For example, the nitrocellulose sheet is subjected to a masking treatment with BSA, skim milk or the like, incubating the sheet with anti-human albumin antibodies and then with enzyme-labeled antibodies and staining the sheet with a reagent such as the combination of an aqueous solution of hydrogen peroxide with diaminobenzidine.

The general assay procedures of the electrofocusing, the transfer and the staining, are summarized below, but the present invention is not particularly limited thereby.

First of all, a sample solution is prepared by adding carrier ampholyte and glycerin to a certain amount of test patient's urine. Then, a certain amount of the sample solution is loaded on a lane of polyacrylamide slab gel and subjected to electrofocusing in a sodium hydroxide solution for the cathode side and a phosphoric acid solution for the anode side as electrofocusing buffers.

After the electrofocusing, the gel is equilibrated in a preliminarily cooled acetic acid solution for a certain period. Then, a transfer sheet and the gel are mounted on a blotting apparatus so that the transfer support is positioned at the cathode side and the gel at the anode side to perform the transfer in a transfer bath containing an acetic acid solution at a constant voltage for a certain period under ice cooling.

After the transfer, the transfer sheet is washed with PBS containing TWEEN 20 and subjected to a masking treatment with PBS containing skim milk at a constant temperature for a certain period.

Then, the sheet is incubated with anti-human albumin antibodies diluted with PBS containing BSA at a constant temperature for a certain period.

After the reaction, the transfer support is washed with PBS containing TWEEN 20 and incubated with a certain concentration of enzyme-labeled second antibodies preliminarily diluted with PBS containing BSA at a constant temperature for a certain period to detect the human albumin fragments.

Cellulose Acetate Sheet Electrophoresis Method

In this method, urinary sample of test patient is applied on a cellulose acetate sheet and subjected to electrophoresis. After electrophoresis, the proteins on the cellulose acetate sheet are either transferred to a nitrocellulose sheet or directly immobilized on the cellulose acetate sheet and the human albumin fragments on the sheets are selectively detected by carrying out a specific antigen-antibody reaction.

Cellulose acetate sheets are generally composed of cellulose of which hydroxyl groups are partially or totally substituted with acetyl groups and the sheets are uniformly composed of distributed micropores. Cellulose acetate sheets have various advantages in comparison with other materials such as filter paper, for example, a) they can be made as thin and uniformly porous sheets, b) they enable the assay with a trace amount of sample, c) they substantially do not cause tailing phenomena during the electrophoresis, d) they can definitely separate the components and the like. Particularly, they can achieve sufficient separation of the components with a short mobility, and as a result, they enable shortening of the electrophoresis time and use of smaller supports. Consequently, they enable the electrophoresis apparatus to be made more compact, simultaneous treatment of a large number of samples and assay procedure automation.

For these reasons, the cellulose acetate sheet electrophoresis technique is widely used as a screening method for routine clinical assays such as the serum protein fractionation method. In this respect, conventional cellulose acetate sheets and electrophoresis apparatuses may be used for the present invention.

Various cellulose acetate sheets are commercially available, and especially Titan III (Helena Laboratory Co., Ltd.) is preferable one because it is laminated with a plastic plate on its backside and hence has sufficient strength.

The conditions of the cellulose acetate sheet electrophoresis are not particularly limited and it is preferably carried out by using 0.2 to 0.4M tris/glycine buffer (pH 9.0 to 9.2) in order to obtain a clear separation, while Veronal buffer (pH 8.6) may be used for the present invention.

The urinary sample is applied to the sheet normally in an amount of 0.4 to 1.2 $\mu$l/cm of sheet width, though the amount is not particularly limited so far as the separation of human albumin and the fragments thereof is possible.

The conditions of voltage may be also conventional and the voltage is desirably selected from the range of from 50 to 200 V.

After the electrophoresis, the proteins may be normally transferred to a support such as a nitrocellulose sheet by lying the cellulose acetate sheet on the support and pressing them for several minutes at room temperature. The support may be similar to those used in the SDS-PAGE method and the gel electrofocusing method.

Alternatively, the proteins migrated by the electrophoresis may be directly fixed on the cellulose acetate sheet by adding denaturation reagent of protein to the cellulose acetate sheet after the electrophoresis.

It is necessary to prevent non-specific reactions when the antigen-antibody reaction is carried out on the nitrocellulose sheet or the cellulose acetate sheet, and they may be prevented with the same way as used in the SDS-PAGE method or the gel electrofocusing method.

In case of the cellulose acetate sheet electrophoresis method, it is necessary to enhance the sensitivity of the antigen-antibody reaction because a relatively smaller amount of sample is used. The detection sensitivity may be enhanced by various techniques and it is preferable to use the avidin-biotin technique. That is, after the reaction with anti-human albumin antibodies, the proteins are reacted with biotinylated second antibodies preparing biotin coupled with the second antibodies and then reacted with enzyme-labeled avidin. The biotinylated antibodies and the enzyme-labeled avidin are commercially available form several manufacturers such as Cappel Co., Ltd. and Zymed Co., Ltd.

The reagent other than avidin and biotin may be the same as those used in the SDS-PAGE method and the gel electrofocusing method.

The assay procedure of the cellulose acetate sheet electrophoresis, the transfer, and the staining are summarized below, but the procedure of the cellulose acetate sheet electrophoresis method according to the present invention is not limited thereby.

First of all, a certain amount of test patient's urine is applied with an applicator to a cellulose acetate sheet, which has been preliminarily equilibrated with an electrophoresis buffer.

Then, the sheet is mounted on a commercially available electrophoresis apparatus wherein tris/glycine buffer and sodium barbital/boric acid buffer are provided for the anode side and the cathode side respectively and subjected to electrophoresis under a constant voltage.

After the electrophoresis, the cellulose acetate sheet is lain on a nitrocellulose sheet, which is preliminarily equilibrated with a glycine/tris buffer containing methanol, and they are pressed for several minutes.

The transferred human albumin and fragments thereof on the nitrocellulose sheet are incubated with anti-human albumin antibodies at a constant temperature for a certain period.

Then, the nitrocellulose sheet is washed with PBS containing surfactant and incubated with biotinylated anti-IgG antibodies at a constant temperature for a certain period.

After washing, the nitrocellulose sheet is incubated with enzyme-labeled avidin at a constant temperature for a certain period, washed again and stained with a reagent to detect the presence of the human albumin fragments.

The general procedure of the cellulose acetate sheet electrophoresis, the direct immobilization of the human albumin and the fragments thereof on the cellulose acetate sheet and the selective detection of the human albumin and the human albumin fragments by staining are summarized below, but the procedure of the cellulose acetate sheet electrophoresis method including the direct immobilization of the protein according to the present invention is not limited thereby.

A certain amount of urinary sample of a test patient is applied with an applicator on a cellulose acetate sheet, which has been preliminarily equilibrated with an electrophoresis buffer.

Then, the sheet is mounted on a commercially available electrophoresis apparatus wherein tris/glycine buffer and sodium barbital/boric acid buffer are provided for the anode side and the cathode side respectively and the sheet is subjected to electrophoresis under a constant voltage.

After the electrophoresis, the cellulose acetate sheet is treated with trichloroacetic acid/sulfosalicylic acid solution to immobilize the human albumin and the fragments thereof on the sheet.

Then, the sheet is washed with distilled water, incubated with anti-human albumin antibodies at a constant temperature for a certain period, washed with PBS containing a surfactant and incubated with biotinylated anti-IgG antibodies at a constant temperature for a certain period.

After washing, the sheet is incubated with enzyme-labeled avidin at a constant temperature for a certain period, washed again and stained with a reagent to detect the presence of the human albumin fragments.

Liquid Chromatographic Method

As stated hereinbefore, the method of the present invention may be carried out by liquid chromatography techniques.

Recently, remarkable progress has been made in the field of analysis of biological components by liquid chromatography. Especially, in the field of high performance liquid chromatography (HPLC), there has been made remarkable improvements such as increase of theoretical plate, improvements of quantitative pump and detector as well as developments of apparatuses for complete automatization of the analysis process such as autosamplers and autoinjector systems and, as a result, it has become possible to carried out day-and-night analysis by HPLC.

On the other hand, more accurate and more rapid analysis is always desired in the clinical test field, and therefore the HPLC system has become an indispensable assay system in certain clinical tests such as the analysis of hemoglobin $A_{IC}$ of which value is regarded as an index of variation of blood sugar level of diabetes mellitus patients within past few months.

When the albumin fragments in urine are analyzed by liquid chromatography techniques including HPLC, while it is possible to separate variously complex components in urine all at once in a single column, it is also possible to use two columns, i.e., a pre-column and a main column, so that the albumin and the fragments thereof are preliminarily adsorbed in the pre-column to separate from the other components, then eluted with an eluent and further separated and analyzed by the main column used as a separation column in order to improve the separation efficiency.

The liquid chromatography techniques, which may be used in the present invention, include adsorption chromatography, ion-exchange chromatography, partition chromatography, gel filtration chromatography, affinity chromatography and the like. The separation and analysis of the albumin fragments in urine may be achieved either by any of those techniques or any combination of those techniques.

The procedure for carrying out the present invention by a combination of affinity chromatography with gel filtration will be described hereinafter, but the present invention is not particularly limited thereby.

In order to obtain a mixture of these proteins from urine of a test subject, the affinity chromatography coupled with anti-human albumin antibody is advantageously used for the separation of human albumin and the fragments thereof.

The antibodies to the human albumin and the fragments thereof are covalently bound to a carrier, which is usually selected from activated polysaccharides such as activated agarose obtained by treating polysaccharides such as agarose with cyanogen halogenide such as cyanogen bromide (BrCN), via amino groups of the proteins (Axen, R., Porath, J. & Ernback, S. *Nature*, 214, 1302, 1967).

Various materials including polysaccharides have been reported as the support for affinity chromatography, and the antibodies may be readily bound to such supports. For example, SEPHAROSE 4B (Pharmacia Co., Ltd.) may be reacted with BrCN under an alkaline condition (pH 11 to 12) to prepare BrCN-activated SEPHAROSE 4B. A solution of anti-human albumin antibodies is added to the BrCN-activated SEPHAROSE 4B in the present invention under a condition of pH 8 to 10 and the support for affinity chromatography can be obtained.

When it is desirable to avoid the use of BrCN because of its toxicity, it is also possible to use a commercially available activated support such as CNBr-activated SEPHAROSE 4B (registered trade mark of Pharmacia Co., Ltd.), to which the anti-human albumin antibodies may be readily coupled. In addition, commercially available activated supports for HPLC, which are recently sold on the market, are also useful for the present invention. Examples of the activated supports for HPLC include TSKgel Tresyl-5PW (Toso Co., Ltd.), which is obtained by introducing tresyl groups into a gel containing a hydrophilic polymer, TSKgel G5000PW (Toso Co., Ltd.), and this support may react with primary amine groups or thiol groups of the protein molecules.

The anti-human albumin antibodies used as ligands of affinity chromatography may be either polyclonal antibodies or monoclonal antibodies obtained from any animal species and they may be easily prepared in any labolatory. For example, anti-human albumin antibodies with a higher purity may be obtained by purifying antiserum of a rabbit immunized with human albumin through an affinity, chromatography column such as a human albumin-SEPHAROSE 4B column.

The mixture of human albumin and the fragments thereof obtained from the affinity chromatography may be further separated into human albumin and the fragments thereof by gel filtration chromatography.

Gel filtration chromatography using a carrier such as SEPHADEX (Pharmacia Co., Ltd.) may be used for the present invention, but it is sometimes undesirable because it requires a large amount of sample, it takes rather long operating time and the reproducibility of this technique is not always excellent.

On the other hand, HPLC techniques are very advantageous since they enable to carry out the analysis with a small amount of sample in a short time to give analytical results with good reproducibility.

While TSKgel (Toso Co., Ltd.), Nucleonics Co., Ltd.), CPG-10 (Electro-Nucleonics Co., Ltd.), Protein Column I-125 (Waters Co., Ltd) and the like can be used as examples of commercially available supports for HPLC of proteins, the most preferred carrier is TSKgel because different supports functioning various exclusion limits with respect to the molecular weight are sold on the market. For example, TSKgel G3000SW and TSKgel G3000SWxL function a exclusion limit molecular weight of 500kDa, and TSKgel G2000SW and TSKgel G2000SWxL function 100 kDa, and these are suitable for the separation of human albumin (molecular weight, 69,000) and the fragments thereof.

The assay procedure of the liquid chromatography is summarized below, but the present invention is not limited thereby.

Urinary sample of a test subject in a certain amount is adsorbed on a support coupling anti-albumin antibodies and eluted to obtain a mixture of human albumin and the fragments thereof under an acidic condition. The obtained mixture is directly loaded on the high performance gel filtration chromatography to obtain an elution pattern by monitoring the ultraviolet absorbance (A280 nm). If higher detection sensitivity is desired, the elution pattern of high performance gel filtration chromatography may be obtained from fluorescence intensity by using an eluent of affinity chromatography reacted with a fluorescent reagent such as FITC.

EXAMPLES

The present invention is illustrated more in detail hereinafter with reference to the following non-limitative working examples. All percentages used in the descriptions of the examples are by weight.

Example 1: Detection of human albumin fragments in urine by the SDS-PAGE method

SDS-PAGE

Solubilization of urine

Urinary sample was added to the same amount of 20 mM tris/HCl buffer (pH 6.8) containing 2% SDS, 2% 2-mercaptoethanol and 40% glycerin and solubilized in boiled water bath for 5 minutes.

Electrophoresis

Electrophoresis was carried out according to the method of Laemmli by using 4% polyacrylamide gel (SDS-PAGE mini, Tefco Co., Ltd.) for the concentration gel and 12% of the same gel for the separating gel. 10μl of the solubilized test urine was loaded on a lane of the gel and subjected to electrophoresis at 20 mA for 1.5 hours in 380 mM glycine/50mM tris buffer (pH 8.3) containing 0.1% SDS.

Immunoblot

Transfer

After the electrophoresis, proteins were transferred from the polyacrylamide gel to a nitrocellulose sheet (Tefco Co., Ltd.) according to the method of Towbin et al. That is, the gel after the electrophoresis was equilibrated in a preliminarily cooled transfer buffer (190 mM glycine/25 mM tris buffer containing 20% methanol, pH 8.3) for 30 minutes. Then, the gel and the nitrocellulose sheet were mounted on a blotting apparatus wherein the transfer bath was filled up preliminarily with the cooled transfer buffer so that the polyacrylamide gel was positioned at the cathode side and the nitrocellulose sheet at the anode side. Transfer was carried out at 42 V for 2 hours under ice cooling.

Detection of human albumin fragments

After the transfer, the nitrocellulose sheet was washed 3 times with 0.05% TWEEN 20/PBS (pH 7.2) and subjected to a masking treatment with 3% skim milk/PBS at 4° C. overnight. Then the sheet was incubated with rabbit anti-human albumin antiserum (MBL Co., Ltd) diluted in a ratio of 1:200 with 1% BSA/PBS at room temperature for 1 hour. After the incubation, the sheet was washed 3 times with 0.05% TWEEN 20/PBS and incubated with HRPO anti-rabbit IgG antibodies (Cappel Co., Ltd.) diluted in a ratio of 1:400 with 1% BSA/PBS at room temperature for 1 hour.

After the washing, the sheet was stained with 0.007% aqueous solution of hydrogen peroxide and 0.05M tris/HCl buffer (pH 7.2) containing 0.025% of 3,3'-diaminobenzidine (K. Ogata et al., *Clinical Pathology*, 31, 215, 1983). The reaction was stopped with distilled water and the presence of the human albumin fragments was detected.

When the assay was carried out on urinary sample of a healthy control subject, only a single band of the native albumin (molecular weight, 69,000) was detected and no fragment of human albumin was detected.

Detection of human albumin fragments was carried out on each of urinary samples from 5 healthy control subjects, 9 patients of IgA nephropathy, 4 patients of diabetic nephropathy and 9 patients of diabetes mellitus in the same way as described above.

The immunoblot patterns of the urinary samples of the healthy control subject are shown in FIG. 1. Every urinary sample from the 5 healthy control subjects showed a single band corresponding to native human albumin (molecular weight, 69,000).

Figure 2:
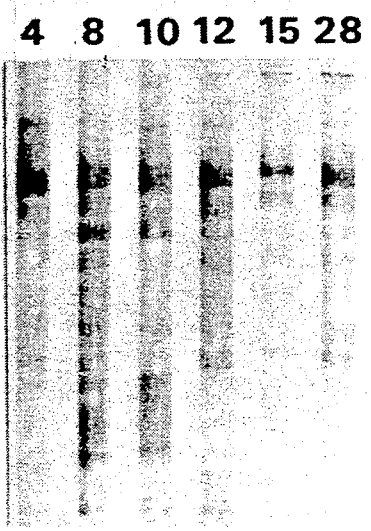
FIG. 2 is a photograph showing immunoblot patterns of urinary samples of 6 IgA nephropathy patients analyzed by the present method (SDS-PAGE method).

The immunoblot patterns of the urinary samples from the IgA nephropathy patients are shown in FIG. 2. In all of the urinary samples of the 6 patients, human albumin fragments were detected in a molecular weight range lower than the native human albumin (69,000).

Figure 3:
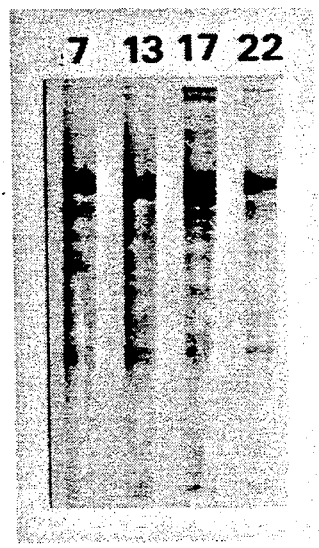
FIG. 3 is a photograph showing immunoblot patterns of urinary samples of 4 diabetic nephropathy patients analyzed by the present method (SDS-PAGE method)

The immunoblot patterns of the urinary samples from the diabetic nephropathy patients are shown in FIG. 3. In all of the urinary samples of the 4 patients, human albumin fragments were detected in a molecular weight range lower than the native human albumin (69,000).

Figure 4:
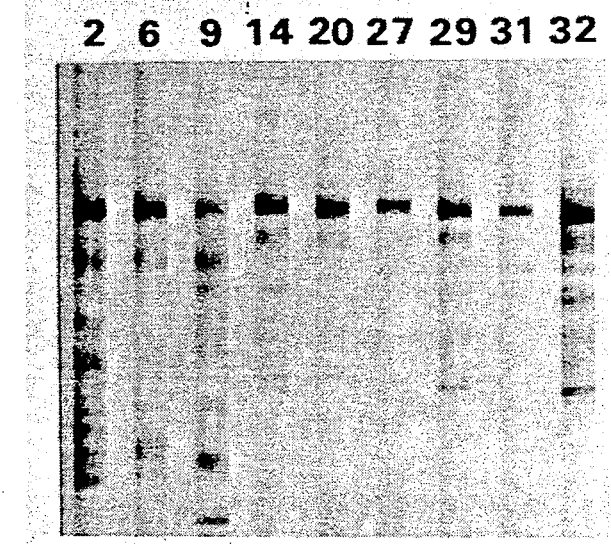
FIG. 4 is a photograph showing immunoblot patterns of urinary samples of 9 diabetes mellitus patients analyzed by the present method (SDS-PAGE method).

The immunoblot patterns of the urinary samples from the diabetes mellitus patients were shown in FIG. 4. On 6 urinary samples in the 9 samples, human albumin fragments were detected in a molecular weight range lower than the native human albumin (69,000).

COMPARATIVE EXAMPLE

Detection of microalbumin was carried out on each of the same urinary samples as used in Example 1 by using commercial kits for detecting microalbumin (ALBUSURE, Eisai Co., Ltd.), and the results were compared with those of Example 1.

Results of Example 1 and Comparative Example are summarized in Table 1 below.

TABLE 1

Comparison of the present invention method with microalbumin method

| | Number of Positive Sample/Number of Sample | | | |
|---|---|---|---|---|
| | IgA nephropathy | Diabetic nephropathy | Diabetes mellitus | Healthy control subject |
| SDS-PAGE method | 6/6 | 4/4 | 6/9 | 0/5 |
| ALBUSURE ® | 5/6 | 4/4 | 0/9 | 0/5 |

All of the samples from IgA nephropathy patients gave positive results in the assay of the present invention, whereas one of them gave a negative result in the ALBUSURE ® assay.

6 samples from diabetes mellitus patients in 9 samples gave positive results in the assay according to the present invention, whereas none of them gave a positive result in the Albusure ® assay.

All of the samples from healthy control subjects gave no positive result both in the present invention and the ALBUSURE ® assay.

These results indicate that the method of the present invention exhibits a higher sensitivity in detecting various nephropathies than that of the ALBUSURE ® assay and it is particularly useful for diagnosing diabetic nephropathy in its earlier stage.

Example 2: Detection of human albumin fragments in urine by the electrofocusing method Urinary sample was diluted 5 times with a sample buffer. The sample buffer was preliminarily prepared according to the following formulation.

| | |
|---|---|
| Servalyt (a carrier for electrofocusing, available from Serva Co., Ltd., pH 3–10) | 0.2 ml |
| Glycerin | 3.0 ml |
| Distilled water | Remains |
| Total | 10 ml |

10 μl of the above obtained urinary sample was loaded on a lane of IEF PAGE mini (Tefco Co., Ltd., pH 3-10) and subjected to electrophoresis with stepwise increasing voltage, i.e., initially at 100 V for 30 minutes, then 200 V for 30 minutes and then 500 V for 60 minutes using 0.05M NaOH for the cathode and 0.01M $H_3PO_4$ for the anode as the electrophoresis buffers.

After the electrophoresis, the gel was equilibrated in preliminarily cooled 0.5% acetic acid for 30 minutes The gel and a nitrocellulose sheet (S & S Co., Ltd.) were mounted on a blotting apparatus of which transfer bath was filled up with cooled 0.5% acetic acid so that the nitrocellulose sheet was positioned at the cathode side and the polyacrylamide gel at the anode side. Transfer was carried out at 42 V for 2 hours under ice cooling.

After the transfer, the nitrocellulose sheet was washed 3 times with 0.05% TWEEN 20/PBS (pH 7.2) and subjected to a masking treatment with 3% skim milk/PBS at 4° C. overnight. Then, the sheet was incubated with rabbit anti-human albumin antiserum (MBL Co ,Ltd) diluted in a ratio of 1:200 with 1% BSA/PBS at room temperature for 1 hour. After the incubation, the sheet was washed 3 times with 0.05% TWEEN 20/PBS and incubated with HRPO anti-rabbit IgG antibodies (Cappel Co., Ltd.) diluted in a ratio of 1:400 with 1% BSA/PBS at room temperature for 1 hour.

After washing, the sheet was stained with 0.007% aqueous solution of hydrogen peroxide and 0.05M tris/HCl buffer (pH 7.2) containing 0.025% of 3,3'-diaminobenzidine (K. Ogata et al., *Clinical Pathology*, 31, 215, 1983).

After the staining, the sheet was washed with distilled water and the presence of the human albumin fragments was detected.

When the assay was carried out on urinary sample of a healthy control subject, a single band was detected around an isoelectric point (hereinafter referred as "pI") of 4.0 with the same mobility as the native albumin (molecular weight, 69,000).

Detection of human albumin fragments was carried out on each of urinary samples from one healthy control subject, 2 patients of diabetes mellitus and one patient of diabetic nephropathy by the electrofocusing method in the same way as described above.

Figure 5:
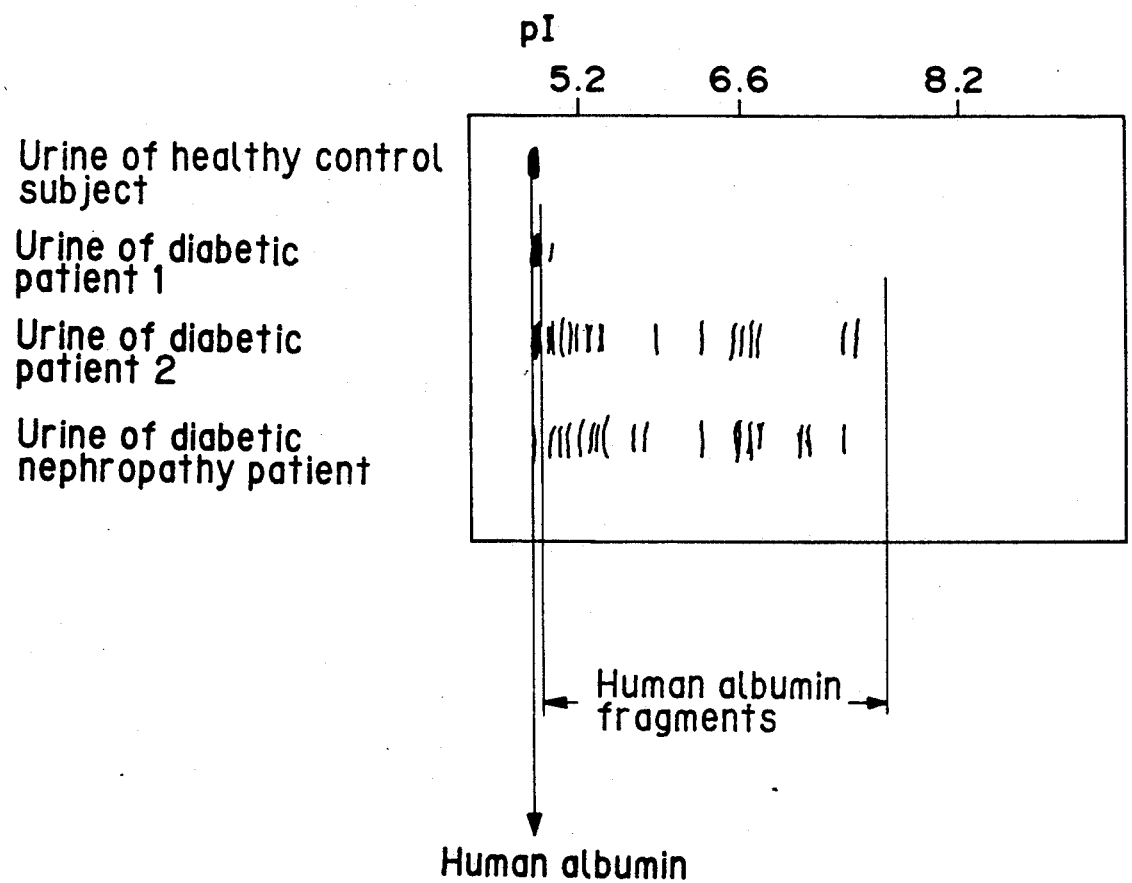
FIG. 5 shows a comparison of albumin and albumin fragments in urinary samples of a healthy control subject and diabetes mellitus patients provided by the present method (gel electrofocusing method).

The results are shown in FIG. 5. The urinary samples of the healthy control subject and the diabetes mellitus patient 1 each showed a single band corresponding to human albumin (molecular weight, 69,000) around a pI of 4.0, whereas the samples from the diabetes mellitus patient 2 and the diabetic nephropathy patient showed several to ten and several bands of the human albumin fragments around a pI range of 5 to 7.

Example 3: Detection of human albumin fragments in urine by the cellulose acetate sheet electrophoresis method including transfer of proteins Electrophoresis Urinary sample of about 1 μl was applied on a cellulose acetate sheet (Taitan III-ZZ, Helena Laboratory Co., Ltd) preliminarily equilibrated in 0.34M tris/glycine buffer (pH 9.1) by means of an applicator (Super Z Applicator, Helena Laboratory Co., Ltd.). Electrophoresis was carried out at 100 V for 45 minutes by using 0.34M tris/glycine buffer (pH 9.1) for the anode and 0.05M sodium barbital/boric acid buffer (pH 8.9, Electra AC buffer, Helena Laboratory Co., Ltd.) for the cathode as the electrophoresis buffers.

Transfer

After the electrophoresis, the cellulose acetate sheet was lain on a nitrocellulose sheet preliminarily equilibrated in 0.19M glycine/0.025M tris buffer containing 20% methanol and pressed at room temperature for 5 minutes to perform the transfer of the proteins.

Staining

The nitrocellulose sheet was incubated with rabbit anti-human albumin antibodies (MBL Co., Ltd.) diluted in a ratio of 1:400 with 1% BSA/PBS at room temperature for 30 minutes.

After the incubation, the sheet was washed 3 times with 0.05% TWEEN 20/PBS and then incubated with biotin-anti-rabbit IgG antibodies (Cappel Co., Ltd.) diluted in a ratio of 1:2000 with 1% BSA/PBS at room temperature for 30 minutes.

Then, the sheet was washed with 0.05% TWEEN 20/PBS and incubated with Streptoavidin-HRPO (Zymed Co., Ltd.) diluted in a ratio of 1:1000 with 1% BSA/PBS at room temperature for 30 minutes.

After the incubation, the sheet was washed with 0.05% TWEEN 20/PBS and stained with 0.007% aqueous solution of hydrogen peroxide and 0.05M tris/HCl buffer (pH 7.2) containing 0.025% 3,3'-diaminobenzidine. After the staining, the sheet was washed with distilled water to detect the presence of the human albumin fragments.

When the detection was carried out on urinary sample of a healthy control subject, a single band with the same mobility as the native human albumin (molecular weight, 69,000) was observed and no fragment of human albumin was detected.

Example 4: Detection of human albumin fragments in urine by the cellulose acetate sheet method including the direct immobilization of proteins on cellulose acetate sheets Electrophoresis Urinary sample of about 1 μl was applied on a cellulose acetate sheet (Taitan III-ZZ, Helena Laboratory Co., Ltd) preliminarily equilibrated in 0.34M tris/glycine buffer (pH 9.1) by means of an applicator (Super Z Applicator, Helena Laboratory Co., Ltd.). Electrophoresis was carried out at 100 V for 45 minutes by using 0.34 M tris/glycine buffer (pH 9.1) for the anode and 0.05M sodium barbital/boric acid buffer (pH 8.9, Electra AC buffer, Helena Laboratory Co., Ltd.) for the cathode as the electrophoresis buffers.

Immobilization of proteins

After the electrophoresis, the sheet was treated with 5% trichloroacetic acid/5% sulfosalicylic acid solution to immobilize the proteins thereon and washed 3 times with distilled water.

Staining

The nitrocellulose sheet was incubated with rabbit anti-human albumin antibodies (MBL Co., Ltd ) diluted in a ratio of 1:400 with 1% BSA/PBS at room temperature for 30 minutes.

After the incubation, the sheet was washed 3 times with 0.05% TWEEN 20/PBS and then incubated with biotin-anti-rabbit IgG antibodies (Cappel Co., Ltd.)

diluted in a ratio of 1:2000 with 1% BSA/pBS at room temperature for 30 minutes.

Then, the sheet was washed with 0.05% TWEEN 20/PBS and incubated with Streptoavidin-HRPO (Zymed Co., Ltd.) diluted with 1% BSA/PBB in a ratio of 1:1000 at room temperature for 30 minutes.

After the incubation, the sheet was washed with 0.05% TWEEN 20/PBS and stained with 0.007% aqueous solution of hydrogen peroxide and 0.05M tris/HCl buffer (pH 7.2) containing 0.025% 3,3'-diaminobenzidine. After the staining, the sheet was washed with distilled water to detect the presence of the human albumin fragments.

When the detection was carried out on urinary sample of a healthy control subject, only a single band with the same mobility as the native human albumin (molecular weight, 69,000) was observed and no fragment of human albumin was detected.

Detection of human albumin fragments was carried out on each of urinary samples from 1 healthy control subject, 2 patients of diabetes mellitus and 1 patient of diabetic nephropathy in the same ways as described in Examples 3 and 4, i.e., by the cellulose acetate sheet electrophoresis method including either the transfer of proteins to nitrocellulose sheets or the direct immobilization of proteins on cellulose acetate sheets and the obtained electrophoresis patterns were compared with each other.

Figure 6:
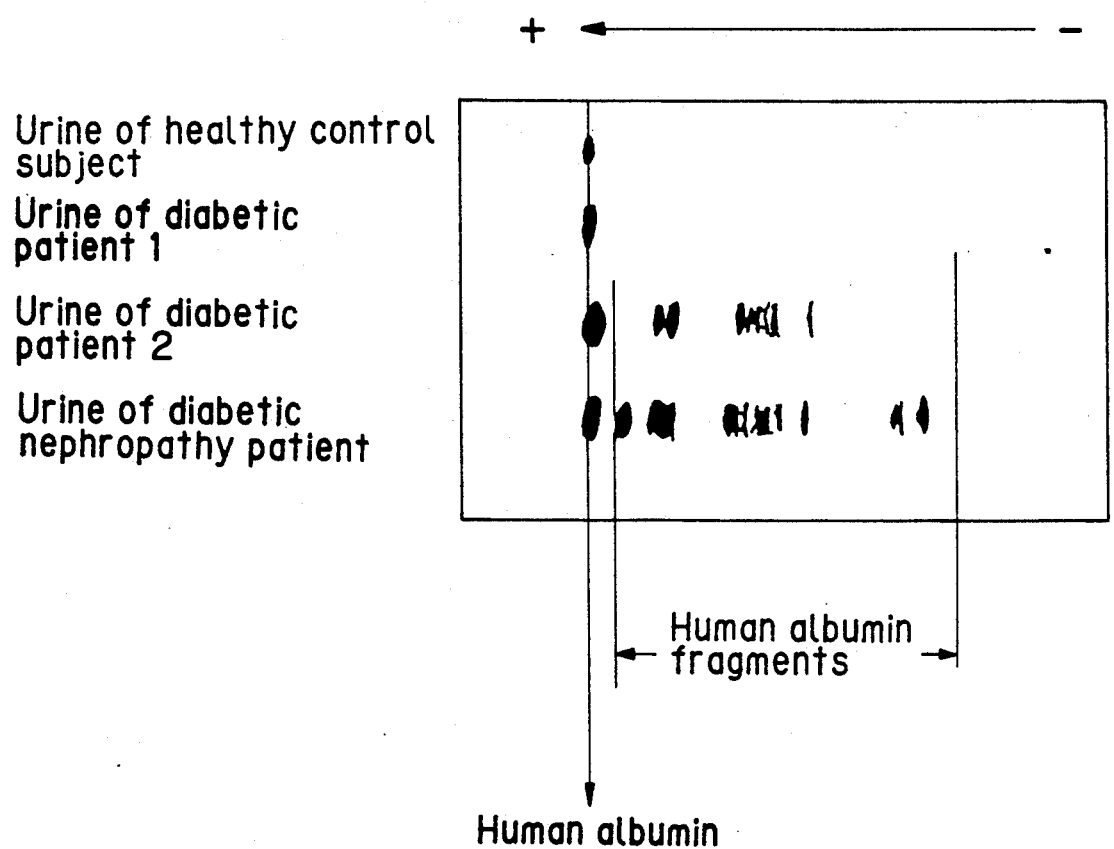
FIG. 6 shows a comparison of albumin and albumin fragments in urinary samples of a healthy control subject and diabetes mellitus patients provided by the present method (cellulose acetate sheet electrophoresis method including immunotransfer).

The immunoblot patterns obtained in the method including the transfer of proteins are shown in FIG. 6. The urinary samples of the healthy control subject and the diabetes mellitus patient 1 each showed a single band corresponding to human albumin (molecular weight, 69,000), whereas the samples from the diabetes mellitus patient 2 and the diabetic nephropathy patient showed a number of bands of the human albumin fragments.

Figure 7:
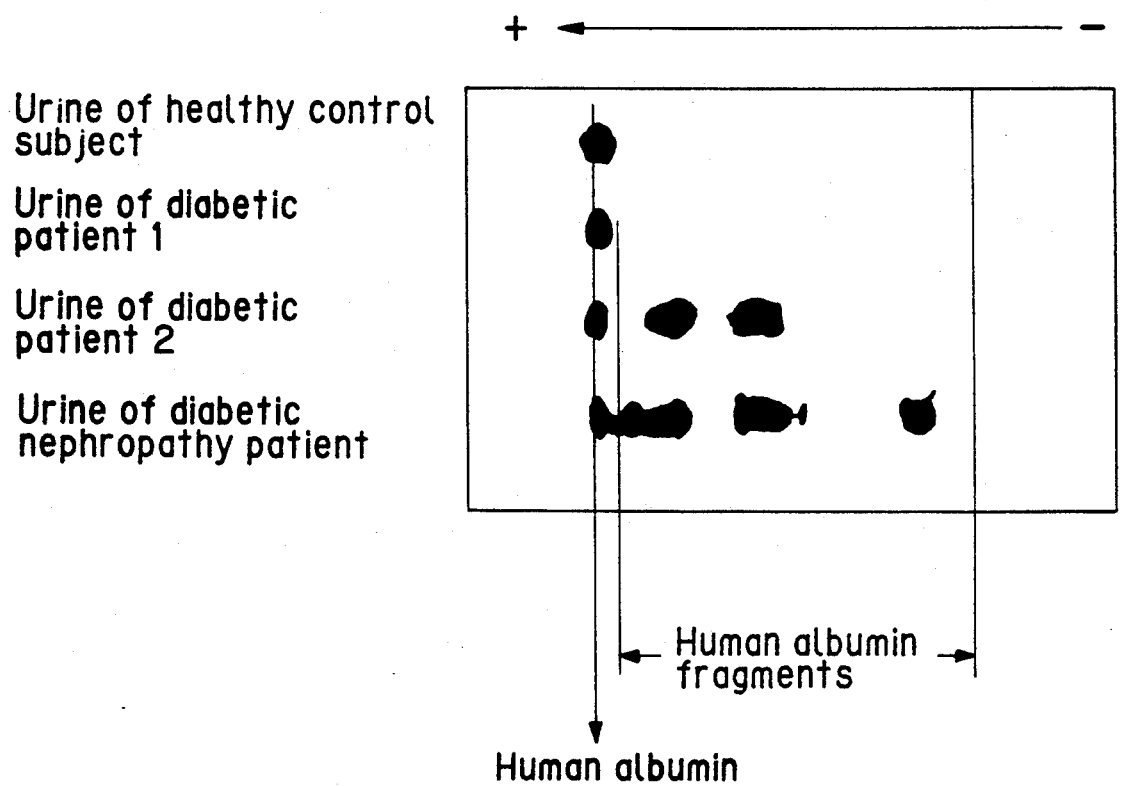
FIG. 7 shows a comparison of albumin and albumin fragments in urinary samples of a healthy control subject and diabetes mellitus and diabetic nephropathy patients provided by the present method (cellulose acetate sheet electrophoresis method including direct immobilization).

The immunoblot patterns obtained in the method including the direct immobilization of proteins are shown in FIG. 7. Though the electrophoresis patterns are similar to those obtained in the method including the transfer of proteins, the bands of the human albumin fragments were obtained as broad bands because of the variations of diffusion degree thereof and differently stained strength.

Example 5: Separation and analysis of human albumin and the fragments thereof (BrCN degradation) by gel filtration chromatography Preparation of standard sample 15 Standard human albumin was obtained as a commercially available product (Cappel Co., Ltd.), which is a chromatographically purified albumin.

The BrCN-fragments of albumin were prepared according to the method of McMenamy et al.(J. Biol. Chem., 246, 4744-4750, 1971) as follows: 1 g of human albumin (Fraction V, Sigma Co., Ltd.) was dissolved in 4 ml of distilled water, added with 16 ml of formic acid and 1 g of BrCN and allowed to react at 4° C. for 24 hours. Then, the reaction mixture was loaded on SEPHADEX G-25 (Pharmacia Co., Ltd.) preliminarily equilibrated in 1% propionic acid and fractions showing absorbance at 280 nm were collected to obtain 800 mg of albumin fragments.

Gel filtration chromatography

A TSKgel G3000SW column (7.5 mm $\phi \times$ 60 cm) was equilibrated with a buffer solution, which was 0.55M glycine/HCl buffer (pH 3.0) containing 0.15M NaCl and 0.1% SDS.

The human albumin and the human albumin fragments were dissolved in the same buffer to prepare 1 mg/ml of solution. Considering the fact that the native albumin molecule consists of 17 S-S bonds, the solution containing 1% 2-mercaptoethanol was separately prepared.

100 μl of each of the samples was loaded on the column and eluted at an elution rate of 0.6 ml/minute and the UV absorbance (A280 nm) was monitored.

Figure 8A:
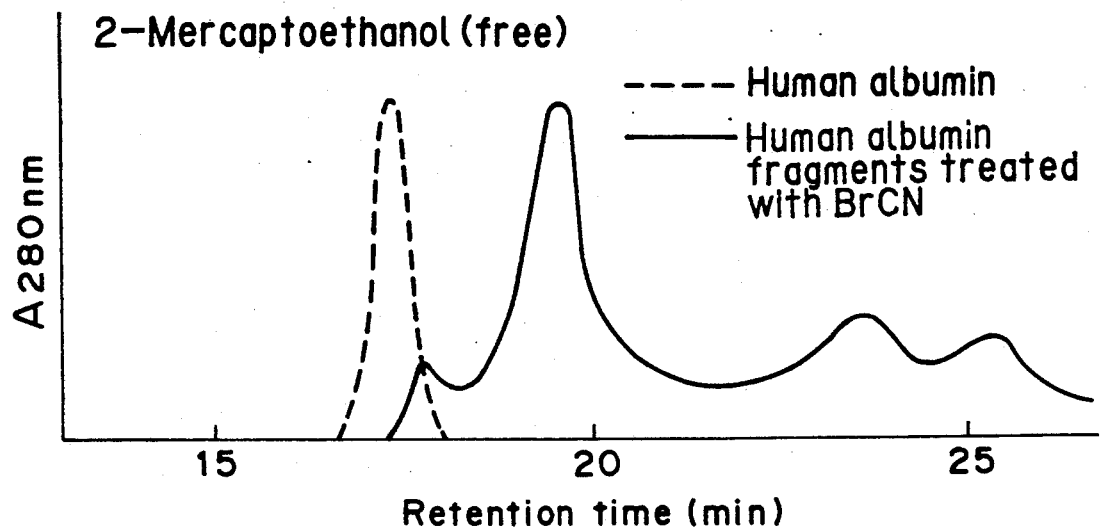
FIGS. 8A and 8B are HPLC chromatograms of human albumin fragments obtained by degrading human albumin with BrCN.
Figure 8B:
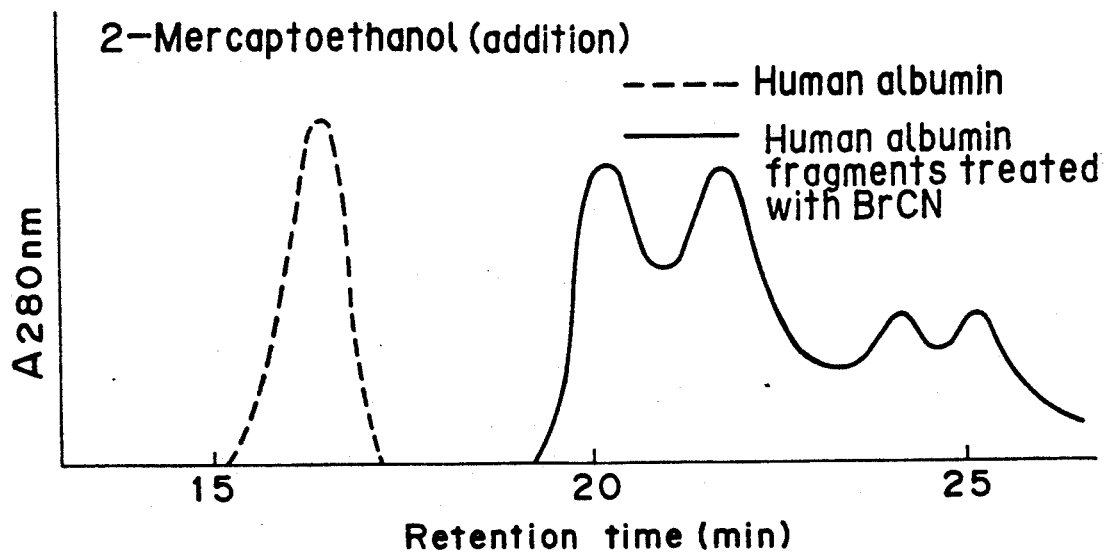
Figure 9A:
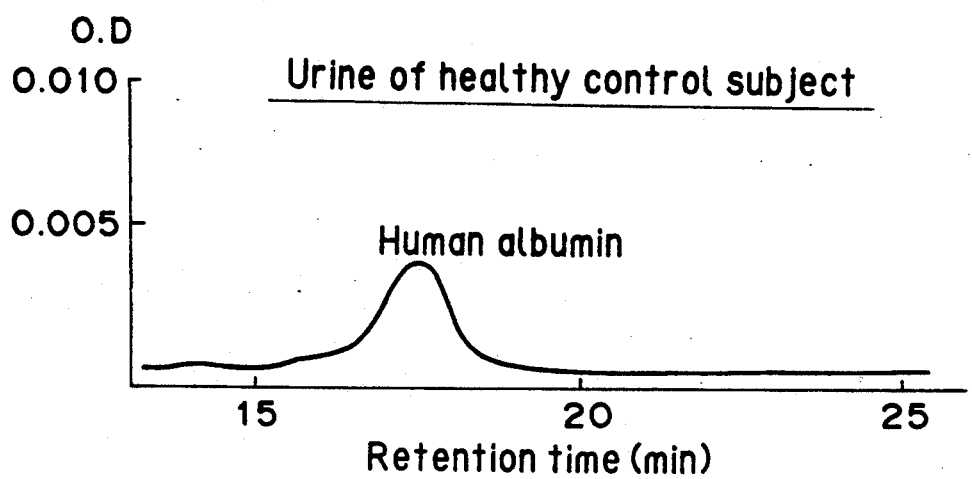
FIGS. 9A to 9F show a comparison of albumin and albumin fragments of a healthy control subject and nephropathy patients provided by the present method (HPLC method).
Figure 9B:
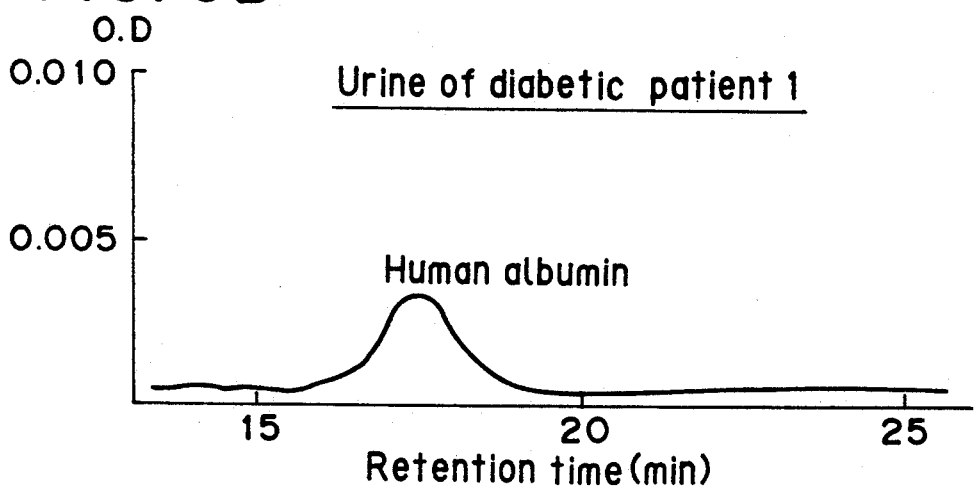
Figure 9C:
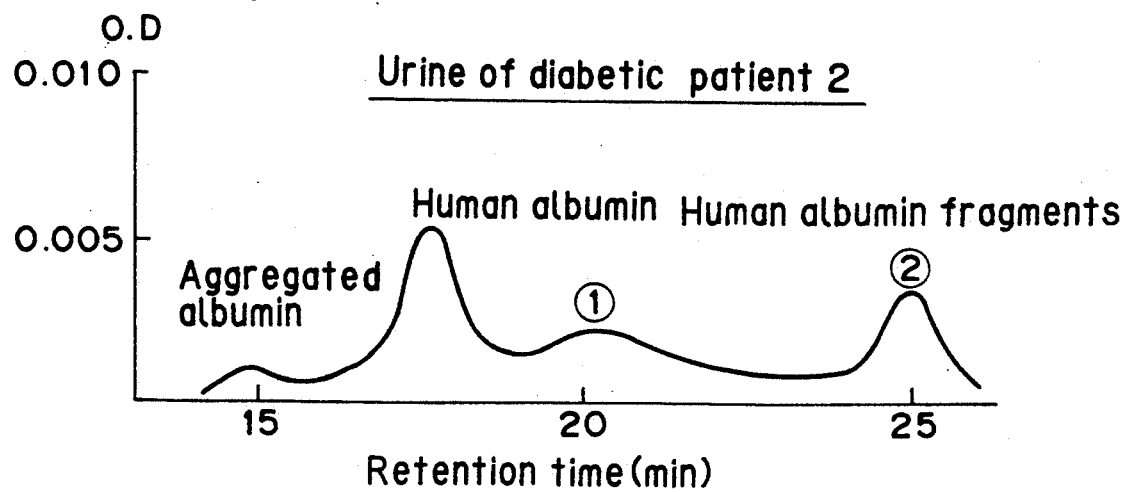
Figure 9D:
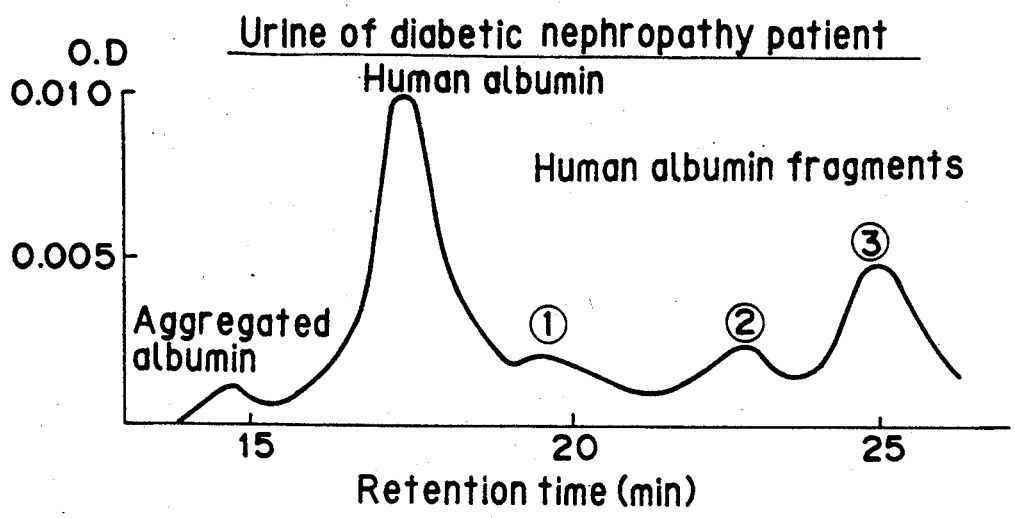
Figure 9E:
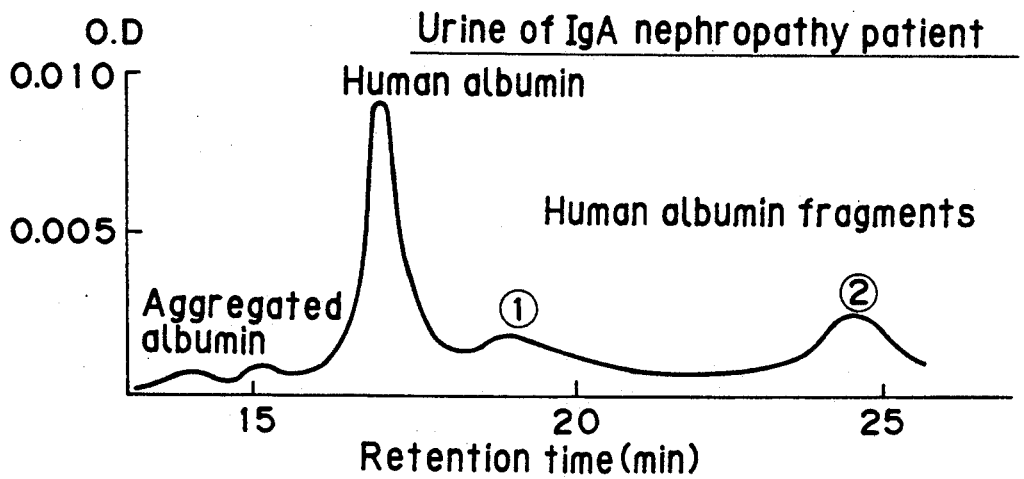
Figure 9F:
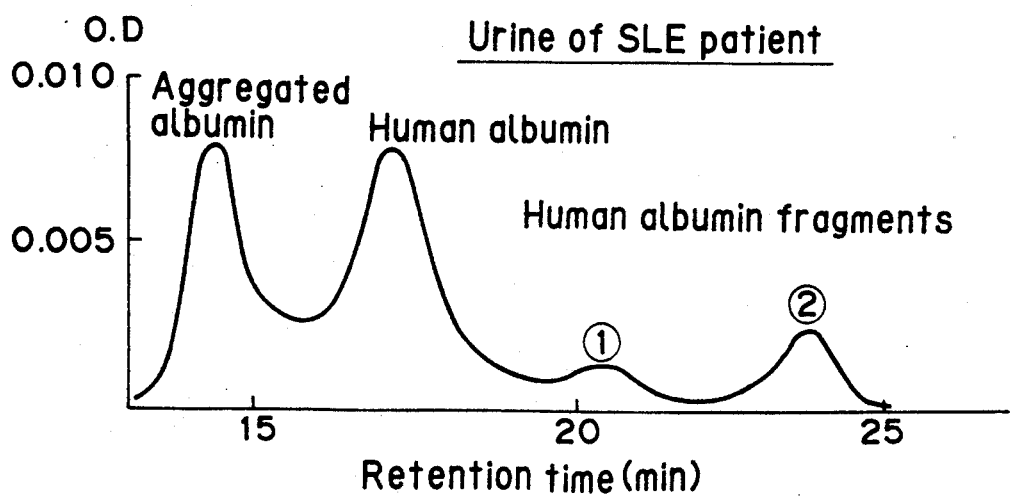

As shown in FIG. 8A, the human albumin was detected as a single peak and the fragments thereof were detected as 4 peaks under the non-reduction. On the other hand, under the reduction, the 4 peaks of the fragments were observed in a lower molecular weight range than that of the non-reduction, and thus the chromatography under reduction showed more clear separation pattern than the non-reduction.

Example 6: Detection of human albumin fragments in urine of nephropathy patients by a combination of affinity chromatography with gel filtration chromatography Preparation of anti-human albumin antibody SEPHAROSE 4B 3 g (corresponding to about 10 ml of gel) of CNBr-activated SEPHAROSE 4B (registered trade mark, Pharmacia Co., Ltd.) was swelled in 1 mM HCl, washed with 500 ml of 1 mM HCl and then washed with 500 ml of 0.1M NaHCO, solution (pH 8.3) containing 0.5M NaCl (hereinafter referred to as "coupling buffer"). Then, the gel was added with 50 mg of rabbit anti-human albumin antibodies purified by affinity chromatography and preliminarily dissolved in the coupling buffer and allowed to react at room temperature for 2 hours.

Then the gel, i.e., the affinity chromatographic support, was washed with 500 ml of coupling buffer, treated with 50 ml of 0.2M glycine solution (pH 8.0) at room temperature for 2 hours to block the remaining active groups and washed with the coupling buffer and 0.55M glycine/HCl buffer (pH 3.0) alternatively to remove excessively adsorbed protein. This support was bound to the anti-human albumin antibodies in an amount of 5 mg/ml of the gel.

Immunoaffinity chromatography

Urinary sample (2 ml) was adsorbed on the anti-human albumin SEPHAROSE 4B equilibrated with 5 mM boric acid buffer (pH 8.0). Then, the support was washed with 5 times in volume of 5 mM boric acid buffer (pH 8.0) and eluted with 0.5M glycine buffer (pH 3.0). Fractions showing UV absorbance (A280 nm) were collected to obtain a mixture of human albumin and human albumin fragments (2 ml).

Separation and analysis of the albumin and the albumin fragments

A TSKgel G3000SW column (7.5 mm $\phi \times$ 60 cm) was equilibrated with a buffer solution, which was 0.55M glycine/HCl buffer (pH 3.0) containing 0.15M NaCl and 0.1% SDS.

To the eluate of the immunoaffinity chromatography (the mixture of the human albumin and the human albumin fragments), SDS was added and the final concentration of SDS in the mixture was prepared to be 0.1%.

100 μl of the mixture was loaded on the column. Elution was carried out at a flow rate of 0.6 ml/minute and the Uv absorbance (A280 nm) was monitored.

Urinary sample

The assay was carried out on urinary samples of 1 healthy control subject, 2 diabetes mellitus patients, 1 diabetic nephropathy patient, 1 IgA nephropathy patient and 1 SLE patient and the results are shown in FIG. 9A to 9F. The urinary samples of the healthy control subject and the diabetes mellitus patient 1 each showed a single peak corresponding to human albumin (molecular weight, 69,000), whereas the samples from the diabetes mellitus patient 2 showed a number of peaks of the human albumin fragments.

Albumin fragments were also significantly detected in urinary samples of the diabetic nephropathy patient, the IgA nephropathy patient and the SLE patient.

Example 7: Detection of human albumin and fragments thereof in urine of nephropathy patients by a combination of affinity chromatography with gel filtration chromatography Preparation of anti-human albumin TSKgel 5PW To 0.5 g of TSKgel Tresyl-5PW, 2 ml of 1.0M potassium phosphate and 20 mg of rabbit anti-human albumin antibodies were added and the mixture gel was shaken in an Erlenmeyer flask for 16 hours to immobilize the antibodies. The amount of the antibodies immobilized on the gel corresponded to 9 mg/ml of the gel.

A high performance immunoaffinity column was prepared by packing anti-human albumin TSKgel 5pW gel (1.0 ml) into a column (10 mm φ×20 mm) under reduced pressure by an aspirator. The amount of the bound antibodies in the column was 2 mg/ml of the gel.

Purification of human albumin and fragments thereof by anti-human albumin TSKgel 5PW The anti-human albumin TSKgel 5PW column (10 mm φ×20 mm) was mounted on an HPLC apparatus and washed with 0.1M phosphate buffer (pH 7.4) at a flow rate of 2.0 ml/minute. Urinary sample in an amount of 50 to 100 μl was loaded on the column and eluted with 0.1M citric acid/HCl (pH 1.6) to complete the elution within 10 minutes.

Separation of human albumin and fragments thereof by TSKgel G3000SW

A TSKgel G3000SW column (7.5 mm φ×60 cm) was equilibrated with a buffer solution, which was 0.55M glycine/HCl buffer (pH 3.0) containing 0.15M NaCl and 0.1% SDS.

To the eluate of the immunoaffinity chromatography (the mixture of human albumin and human albumin fragments), of which pH value was adjusted at 3.0, SDS was added and the final concentration of SDS in the mixture was prepared to be 0.1%. 100 μl of the mixture was loaded on the column. Elution was carried out at a flow rate of 0.6 ml/minute and the UV absorbance (A280 nm) was monitored.

The assay was carried out on urinary samples of 1 healthy control subject, 2 diabetes mellitus patients, 1 diabetic nephropathy patient, 1 IgA nephropathy patient and 1 SLE patient and the same results as Example 6 were obtained.

What is claimed is:

1. A method of diagnosing diabetic or IgA nephropathy of an early stage comprising:
   (a) obtaining a urine sample of a patient suspected of being at an early stage of nephropathy, which urine sample does not contain sufficient microalbumin to obtain a positive result in a microalbumin test;
   (b) separating all of the proteins contained in the urine sample or immunologically recovering albumin and albumin fragments from the urine sample;
   (c) testing the sample from (b) for the presence of albumin fragments by immunologically identifying albumin fragments in the separated proteins or by chromatographically identifying any recovered albumin fragments; and
   (d) detecting the presence of albumin fragments in the sample, wherein the detection of albumin fragments is indicative of an early stage of nephropathy.

2. The method of claim 1, wherein the test for the presence of the albumin fragments comprises immunologically identifying albumin fragments and electrophoresis.

3. The method of claim 2, wherein the immunological technique is selected from the group consisting of immunoassay and immunoblot.

4. The method of claim 3, wherein the immunological technique is immunoblot.

5. The method of claim 2, wherein the electrophoresis is SDS-polyacrylamide gel electrophoresis (SDS-PAGE).

6. The method of claim 2, wherein the electrophoresis is cellulose acetate electrophoresis.

7. The method of claim 2, wherein the electrophoresis is electrofocusing.

8. The method of claim 4, wherein the immunological test for the presence of the albumin fragments comprises separating all of the proteins including the albumin fragments from a urinary sample by SDS-PAGE or electrofocusing, transferring the proteins in the gel to a transfer support, incubating the support with anti-human albumin antibodies as first antibodies, incubating the support with enzyme-labeled anti-IgG antibodies as second antibodies and staining the support with an enzyme-detection reagent.

9. The method of claim 4, wherein the immunological test for the presence of the albumin fragments comprises separating all of the proteins including the albumin fragments from a urinary sample on a cellulose acetate sheet by electrophoresis, transferring the proteins on the sheet to a transfer sheet, incubating the support with anti-human albumin antibodies as first antibodies, incubating the support with biotinylated anti-IgG antibodies as second antibodies, incubating the support with enzyme-labeled avidin and staining the support with an enzyme-detection reagent.

10. The method of claim 3, wherein the immunological test for the presence of the albumin fragments comprises separating all of the proteins including the albumin fragments from a urinary sample on a cellulose acetate sheet by electrophoresis, directly immobilizing the proteins on the sheet, incubating the sheet with anti-human albumin antibodies as first antibodies, incubating the sheet with bioinylated anti-IgG antibodies as second antibodies, incubating the sheet with enzyme-labeled avidin and staining the support with an enzyme-detection reagent.

11. The method of claim 1, wherein the test for the presence of the albumin fragments comprises liquid chromatography.

12. The method of claim 11, wherein the test for the presence of the albumin fragments comprises gel filtration chromatography or ion exchange chromatography.

13. The method of claim 12, wherein the gel filtration chromatography or the ion exchange chromatography is high performance liquid chromatography.

14. The method of claim 12, wherein the native albumin and the fragments thereof are purified by affinity chromatography before they are detected by the gel filtration chromatography or the ion exchange chromatography.

15. The method of claim 14, wherein anti-human albumin antibodies are used as ligands of the affinity chromatography.

16. The method of claim 12, wherein the support for the gel filtration chromatography or the ion exchange chromatography is selected from those used for separation and analysis of proteins.

17. The method of claim 1, wherein the nephropathy diagnosed is diabetic nephropathy.

18. The method of claim 17, wherein the urine sample is obtained from a patient having diabetic mellitus.

19. The method of claim 1, wherein the nephropathy diagnosed is IgA nephropathy.

* * * * *